US012728410B2

(12) United States Patent
Yang et al.

(10) Patent No.: US 12,728,410 B2
(45) Date of Patent: Sep. 8, 2026

(54) ZN-METAL OXIDE/ZEOLITE CATALYST AND METHODS OF MAKING THEREOF

(71) Applicant: The Regents of the University of California, Oakland, CA (US)

(72) Inventors: Ji Yang, Berkeley, CA (US); Ji Su, Richmond, CA (US)

(73) Assignee: The Regents of the University of California, Oakland, CA (US)

( * ) Notice: Subject to any disclaimer, the term of this patent is extended or adjusted under 35 U.S.C. 154(b) by 142 days.

(21) Appl. No.: 18/603,475

(22) Filed: Mar. 13, 2024

(65) Prior Publication Data

US 2024/0316542 A1 Sep. 26, 2024

Related U.S. Application Data

(60) Provisional application No. 63/491,232, filed on Mar. 20, 2023.

(51) Int. Cl.

| | |
|---|---|
| ***B01J 23/26*** | (2006.01) |
| ***B01J 29/78*** | (2006.01) |
| ***B01J 37/00*** | (2006.01) |
| ***B01J 37/04*** | (2006.01) |
| ***B01J 37/08*** | (2006.01) |
| ***C01B 32/40*** | (2017.01) |
| ***C01B 39/02*** | (2006.01) |
| ***C07C 5/42*** | (2006.01) |

(52) U.S. Cl.

CPC ............. *B01J 29/783* (2013.01); *B01J 23/26* (2013.01); *B01J 37/0036* (2013.01); *B01J 37/04* (2013.01); *B01J 37/08* (2013.01); *C01B 32/40* (2017.08); *C01B 39/026* (2013.01); *C07C 5/42* (2013.01); *B01J 2229/38* (2013.01); *C07C 2529/78* (2013.01)

(58) Field of Classification Search

CPC ...... B01J 29/783; B01J 23/26; B01J 37/0036; B01J 37/04; B01J 37/08; C01B 32/40; C01B 39/026

See application file for complete search history.

(56) References Cited

U.S. PATENT DOCUMENTS

2003/0232721 A1* 12/2003 Zhou .................... B01J 37/0203 502/325

OTHER PUBLICATIONS

Huang, Y. et al., Direct Conversion of Syngas to Light Olefins over a ZnCrOx + H-SSZ-13 Bifunctional Catalyst, 6 ACS Omega 2021 10953-10962 (2021) (Year: 2021).*

Yang et al., "Atomically synergistic Zn—Cr catalyst for iso-stoichiometric co-conversion of ethane and CO2 to ethylene and CO", Nature Communications, https://doi.org/10.1038/s41467-024-44918-8. pp. 1-11, (Jan. 30, 2024).

Pu et al., "Engineering heterogeneous catalysis with strong metal-support interactions: characterization, theory and manipulation", Angew. Chem. Int. Ed., vol. 62, e202212278 (2023).

Gomez et al., "Carbon dioxide reduction in tandem with light-alkane dehydrogenation", Nat. Rev. Chem., vol. 3, pp. 638-649, (2019).

Myint et al., "Reforming and oxidative dehydrogenation of ethane with CO2 as a soft oxidant over bimetallic catalysts", J. Catal., vol. 343, pp. 168-177, (2016).

Guo et al., "Descriptor-based identification of bimetallic-derived catalysts for selective activation of ethane with CO2"; EES Catal., vol. 1, pp. 17-25 (2023).

Li et al., "Oxidative dehydrogenation of light alkanes with carbon dioxide", Green Chem., vol. 23, pp. 689-707 (2021).

Najari et al., "Oxidative dehydrogenation of ethane: catalytic and mechanistic aspects and future trends", Chem. Soc. Rev., vol. 50, pp. 4564-4605 (2021).

Zhao et al., "Controlling reaction-induced loss of active sites in ZnOx/Silicalite-1 for durable nonoxidative propane dehydrogenation", ACS Catal., vol. 12, pp. 4608-4617, (2022).

Schweitzer et al., "Propylene hydrogenation and propane dehydrogenation by a single-site Zn2+ on silica catalyst", ACS. Catal., vol. 4, pp. 1091-1098 (2014).

Zhao et al., "In situ formation of ZnOx species for efficient propane dehydrogenation", Nature, vol. 599, pp. 234-238 (2021).

Liu et al., "In situ spectroscopic characterization and theoretical calculations identify partially reduced ZnO1-x/Cu interfaces for methanol synthesis from CO2", Angew. Chem. Int. Ed., vol. 134, 2022).

Thirumala et al., "Oxidative dehydrogenation of ethane with carbon dioxide overCr2O3/SBA-15 catalysts: the influence of sulfate modification of the support", Appl. Petrochem. Res., vol. 7, pp. 107-118, (2017).

Talati et al., "Oxidative dehydrogenation of ethane to ethylene by carbon dioxide over Cr/TiO2—ZrO2 nanocatalyst: effect of active phase and support composition on catalytic properties and performance", Adv. Powder Technol., vol. 27, pp. 1195-1206 (2016).

Bugrova et al., "Oxidative dehydrogenation of ethane with CO2 over CrOx catalysts supported on Al2O3, ZrO2, CeO2 andCexZr1-xO2", Catal. Today, vol. 333, pp. 71-80 (2019).

Tu et al., "CO2-assisted ethane aromatization over zinc and phosphorousmodified ZSM-5 catalysts", Appl. Catal. B. Environ., vol. 304, pp. 120956 (2022).

Yang et al., "One-Step Alkylation of Benzene with Syngas over Non-Noble Catalysts Mixed with Modified HZSM-5", Ind. Eng. Chem. Res., vol. 58, pp. 13879-1388, (Jul. 12, 2019).

Peeters et al., "Highly Dispersed Snbeta Zeolites as Active Catalysts for Baeyer—Villiger Oxidation: The Role of Mobile, In Situ Sn(II)O Species in Solid-State Stannation", ACS Catalysis, vol. 11, pp. 2819-2830, (2021).

(Continued)

*Primary Examiner* — Randy Boyer

(74) *Attorney, Agent, or Firm* — Womble Bond Dickinson (US) LLP

(57) ABSTRACT

This disclosure provides systems, methods, and apparatus related to catalysts. In one aspect, a catalyst is a ZnxMy/zeolite catalyst, with ½≤x/y≤4, and M being a metal from a group Cr, Mo, and W. Zn is an oxide, M is an oxide, and there are at least some $ZnMO_x$ oxides.

22 Claims, 12 Drawing Sheets

(56) References Cited

OTHER PUBLICATIONS

Liu et al. "Influence of the zeolite surface properties and potassium modification on the Zn-catalyzed CO2-assisted oxidative dehydrogenation of ethane", Applied Catalysis B: Environmental, vol. 304, 120947, (May 2022).
Liu et al., "Highly-Dispersed Zinc Species on Zeolites for the Continuous and Selective Dehydrogenation of Ethane with CO2 as a Soft Oxidant", ACS Catalysy, vol. 11, No. 5, pp. 2819-2830, (Feb. 16, 2021).

* cited by examiner

| | Cr/SSZ-13 | $Zn_1Cr_2$ | $Zn_1Cr_1$ | $Zn_2Cr_1$ | $Zn_3Cr_1$ | $Zn_4Cr_1$ | Zn/SSZ-13 |
|---|---|---|---|---|---|---|---|
| $C_2H_6$ Conversion (%) | 5.10 | 9.50 | 13.3 | 14.7 | 19.8 | 14.4 | 12.2 |
| $CO_2$ conversion (%) | 4.90 | 9.10 | 12.2 | 13.6 | 18.7 | 11.8 | 10.2 |
| $CO_2$ utilization (%) | 96.0 | 96.0 | 92.0 | 92.5 | 94.4 | 81.5 | 83.6 |
| $C_2H_4$ selectivity (%) | 95.4 | 96.0 | 94.0 | 95.0 | 93.0 | 94.0 | 93.0 |
| TOF of $C_2H_4$ formation (mol $mol_{Zn+Cr}^{-1}$ $h^{-1}$) | 0.20 | 0.38 | 0.52 | 0.58 | 0.77 | 0.57 | 0.48 |

Figure 2A

ZN-METAL OXIDE/ZEOLITE CATALYST AND METHODS OF MAKING THEREOF

RELATED APPLICATIONS

This application claims priority to U.S. Provisional Patent Application No. 63/491,232, filed Mar. 20, 2023, which is herein incorporated by reference.

STATEMENT OF GOVERNMENT SUPPORT

This invention was made with government support under Contract No. DE-AC02-05CH11231 awarded by the U.S. Department of Energy. The government has certain rights in this invention.

BACKGROUND

The synergistic effects generated by mixed or supported bifunctional catalysts are often claimed to promote the catalytic performance of traditional heterogeneous catalysts. Recently, the construction of synergistic pair-sites with colocalized metal atoms to facilitate distinct elementary steps in the catalytic reaction has been established as a step toward atomically synergistic bifunctional catalyst development. The interaction between these adjacent metal atoms, similar to the metal-support interaction of traditional heterogeneous catalysts, offers the possibility to modulate their respective electronic structure to further enhance their catalytic activity. However, precisely controlling their colocalization requires a complicated synthesis process with multiple synthesis steps to load single atoms. Moreover, the stability of the well-defined synergistic sites is debatable, especially under harsh reaction conditions such as high reaction temperatures.

Growing $CO_2$ emissions and abundant shale gas reserves have prompted a significant amount of research to explore efficient approaches for co-utilizing the products to produce value-added chemicals. Ethane, the second-largest component of shale gas, is an ideal alternative hydrogen source for $CO_2$ conversion. The co-conversion of ethane and $CO_2$ ($C_2H_6+CO_2 \rightarrow C_2H_4+CO+H_2O$) is a viable alternative to the ethane steam cracking for ethylene production under the goal of net negative $CO_2$ emissions. Further, iso-stoichiometric co-conversion of ethane and $CO_2$ (ICEC) to ethylene and CO is crucial for direct downstream processes such as the hydroformylation reaction to produce aldehyde and polymerization process to produce polyketones.

However, the co-conversion process lacks a viable catalyst for achieving high ethylene selectivity and $CO_2$ utilization simultaneously. Metal-based catalysts suffer from the inevitable cleavage of C—C bonds through dry reforming pathways and lower the ethylene selectivity. Oxide-based catalysts exhibit the great merit of preferential C—H bond scission over C—C bond scission pathways but require excessive $CO_2$ cofeeding to reduce ethane adsorption and scavenge the surface H species.

Specifically, Zn and Cr oxide-based catalysts were widely studied for co-conversion of ethane and $CO_2$. The acidic $Zn^{2+}$ site displayed high activity for C—H bond cleavage in ethane and $CO_2$ activation, requiring the participation of adjacent active sites to form binuclear sites. The challenge is that acidified $Zn^{2+}$—H hydride displays a capacity for C—C bond scission of ethane, leading to undesired production of methane. Redox $Cr^{6+}$ sites require lattice oxygen as a H acceptor to dissociate C—H bonds but trigger the formation of less active $Cr^{3+}$ species. The reoxidation of $Cr^{3+}$ to $Cr^{6+}$ is limited by slow O abstraction from $CO_2$.

SUMMARY

The above analyses indicate the need for an atomically-synergistic binuclear a Zn—O— metal (e.g., Zn—O—Cr) site catalyst for ICEC, with Zn facilitating $CO_2$ adsorption and activation to provide O species for $Cr^{6+}$ regeneration and adjacent Cr as an electron donor reducing the acidity of $Zn^{2+}$ to facilitate its activity and selectivity for C—H bond scission. More generally, exploring a cooperative redox and acid-base catalytic mechanism for ICEC is highly desirable.

Described herein are the fabrication and demonstration of a Zn—O-metal (e.g., Zn—O—Cr) atomically-synergistic binuclear-site catalyst (ABC) that is efficient for ICEC with high ethylene selectivity and utilization of converted $CO_2$ ($U_{CO_2}$). Compared with pure Zn and Cr catalysts, Zn—O—Cr ABC displays ~1.5 and ~4-fold higher catalytic activity with 100% ethylene selectivity and 99.0% $U_{CO_2}$, under optimized reaction conditions. A factor in this high performance is the discovery that Cr facilitates the formation of a $Zn^{\delta+}$ ($0<\delta<2$) site to enhance the β-C—H bond cleavage of ethane, while the resulting Lewis base Zn—$H^{\delta-}$ hydride favors $CO_2$ adsorption and activation, and prevents C—C bond scission of ethane. The redox Cr site accelerates $CO_2$ dissociation and facilitates $H_2O$ formation/desorption. The apparent activation energies of ethane conversion and $CO_2$ conversion are ~70.9 and ~74.0 kJ/mol, which demonstrates the rate matching achieved in ICEC.

One innovative aspect of the subject matter described in this disclosure is a ZnxMy/zeolite catalyst, with ½≤x/y≤4, with M being a metal from a group Cr, Mo, and W, with Zn being an oxide, with M being an oxide, and with at least some $ZnMO_x$ oxides.

Another innovative aspect of the subject matter described in this disclosure can be implemented in a method including mixing a Zn precursor, a metal precursor, and a zeolite to form a mixture. A metal of the metal precursor is a metal from a group Cr, Mo, and W. The mixture is then ground. After grinding the mixture, the mixture is heat treated to form a ZnxMy/zeolite catalyst, with ½≤x/y≤4. Zn is an oxide, M is an oxide, and Zn and M form at least some $ZnMO_x$ oxides.

Another innovative aspect of the subject matter described in this disclosure can be implemented in a method including providing a ZnxMy/zeolite catalyst, with ½≤x/y≤4. M is a metal from a group Cr, Mo, and W. Zn is an oxide, M is an oxide, and there are at least some $ZnMO_x$ oxides. The ZnxMy/zeolite catalyst is heated to about 400° C. to 650° C. Carbon dioxide and ethane are flowed through the ZnxMy/zeolite catalyst to generate carbon monoxide and ethylene.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

FIG. 2A shows a table that includes the catalytic performance of Zn—O—Cr ABCs (Reaction conditions: Temperature=550° C.; Reactant composition=5% $C_2H_6$+5% $CO_2$+90% Ar; WHSV=7500 mL $$g_{cat}^{-1}$$

FIG. 3A, C1s spectra; FIG. 3B, Auger spectra of Zn LMM; and FIG. 3C, Cr 2p3/2 spectra as a function of reaction conditions for $Zn_3Cr_1$/SSZ-13. T=550° C.: ultra-high vacuum (UHV), $C_2H_6$ (50 mTorr)+$CO_2$ (50 mTorr), $C_2H_6$ (100 mTorr), and $CO_2$ (100 mTorr) in sequence.

FIG. 4A shows an illustration of the catalytic cycles of ICEC over binuclear Zn—O—Cr sites of $Zn_3Cr_1$/SSZ-13. FIG. 4B shows an illustration of the calculated energy profiles of ICEC on $Zn_3Cr_1$/SSZ-13, Zn/SSZ-13, and Cr/SSZ-13.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

The terms "about" or "approximate" and the like are synonymous and are used to indicate that the value modified by the term has an understood range associated with it, where the range can be ±20%, ±15%, ±10%, ±5%, or ±1%. The terms "substantially" and the like are used to indicate that a value is close to a targeted value, where close can mean, for example, the value is within 80% of the targeted value, within 85% of the targeted value, within 90% of the targeted value, within 95% of the targeted value, or within 99% of the targeted value.

Figure 5:
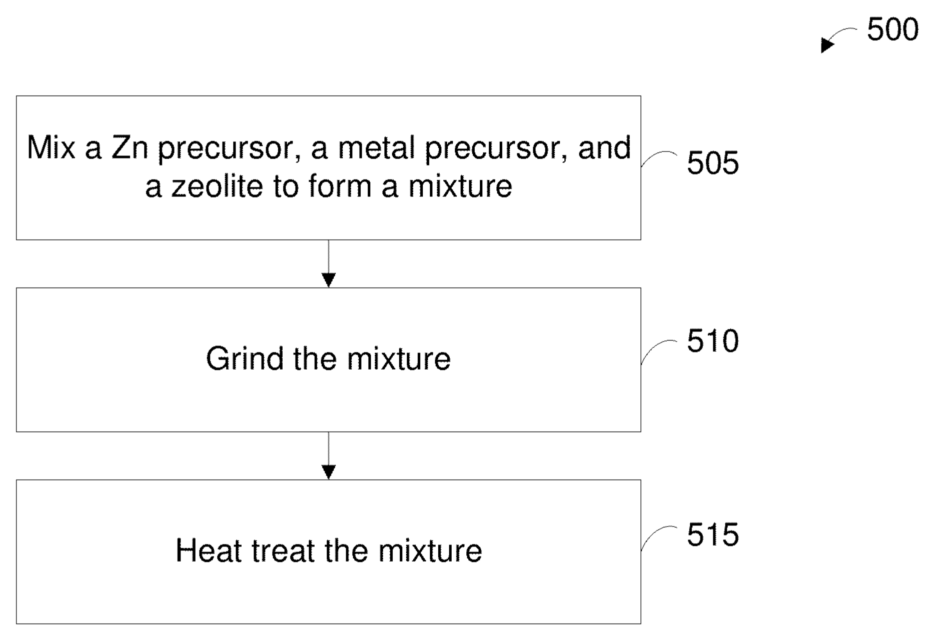
FIG. 5 shows an example of a flow diagram illustrating a manufacturing process for an Zn-metal oxide/zeolite catalyst.
Figure 6:
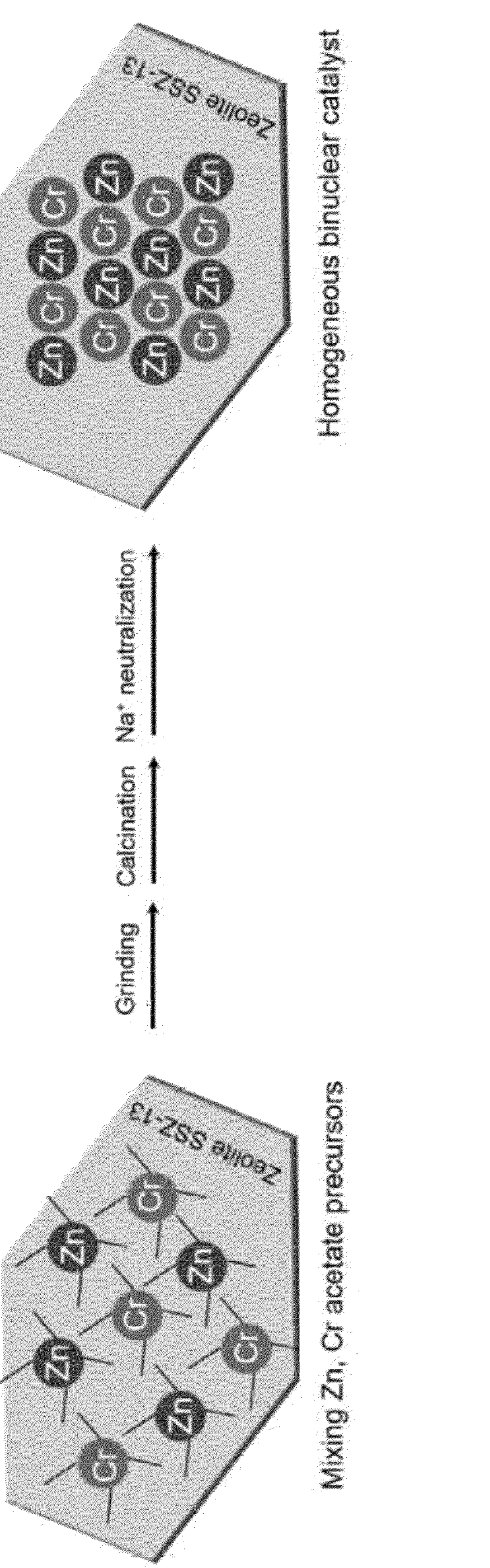
FIG. 6 shows an example of a schematic illustration of a manufacturing process from a Zn—Cr oxide/SSZ-13 zeolite catalyst.

FIG. 5 shows an example of a flow diagram illustrating a manufacturing process for an Zn-metal oxide/zeolite catalyst. FIG. 6 shows an example of a schematic illustration of a manufacturing process from a Zn—Cr/SSZ-13 zeolite catalyst. Starting at block 505 of the process 500 shown in FIG. 5, a Zn precursor, a metal precursor, and a zeolite are mixed to form a mixture. A metal of the metal precursor is a metal from a group Cr, Mo, and W.

In some embodiments, the Zn precursor is a Zn precursor from a group zinc (II) acetate, zinc (II) nitrate, and zinc (II) chloride. In some embodiments, the Cr precursor is a Cr precursor from a group chromium (III) acetate hydroxide, chromium (III) nitrate, and chromium (III) chloride. In some embodiments, the Mo precursor comprises or essentially consists of ammonium molybdate tetrahydrate. In some embodiments, the W precursor comprises or essentially consists of ammonium metatungstate hydrate.

In some embodiments, the salt of the Zn precursor and the salt of the metal precursor are the same salts. For example, zinc (II) nitrate and chromium (III) nitrate. In some embodiments, the salt of the Zn precursor and the salt of the metal precursor are different salts. For example, zinc (II) nitrate and chromium (III) chloride.

In some embodiments, the zeolite is a zeolite from a group HSSZ-13 zeolite, NaSSZ-13 zeolite, HZSM-5 zeolite, NaZSM-5 zeolite, H-ZSM-11 zeolite, H-ZSM-22 zeolite, H-ZSM-23 zeolite, ZSM-35 zeolite, Beta zeolite, SAPO-11 zeolite, and SAPO-34 zeolite. In some embodiments, the zeolite comprises a SSZ-13 zeolite.

At block 510, the mixture is ground. In some embodiments, the grinding is performed with a ball mill. In some embodiments, the grinding is performed with a mortar and pestle.

In some embodiments, the Zn precursor and the metal precursor each have a particle size of less than about 0.5 nanometers after the grinding. In some embodiments, the zeolite has a particle size of about 1 micron to 2 microns after the grinding.

At block 515, after grinding the mixture, the mixture is heat treated to form a ZnxMy/zeolite catalyst, with $\frac{1}{2}\le x/y\le 4$, with Zn being an oxide, with M being an oxide, and with Zn and M forming at least some $ZnMO_x$ oxides. In some embodiments, the heat treatment comprises heating the mixture to about 300° C. to 800° C., or about 550° C., for about 1.5 hours to 4.5 hours, or about 3 hours. In some embodiments, the heat treatment is performed in an inert atmosphere. In some embodiments, the heat treatment is performed under flowing nitrogen.

In some embodiments, the $ZnMO_x$ oxides are solid solution oxides. That is, the Zn, M, and oxygen form a solid solution. In some embodiments, the $ZnMO_x$ oxides have a structure of $Zn^{\delta+}$—O-$M^{\delta+}$ ($0<\delta<2$). In some embodiments, the catalyst is a $Zn_3M_1$/zeolite catalyst. In some embodiments, the catalyst is a $Zn_3Cr_1$/SSZ-13 catalyst.

In some embodiments, only $ZnMO_x$ oxides are formed, and no Zn oxides or metal oxides are formed. In some embodiments, only dispersed $ZnMO_x$ oxides with a structure of $Zn^{\delta+}$—O-$M^{\delta+}$ ($0<\delta<2$) are formed, and no Zn oxides or metal oxides are formed. This is the case, for example with $Zn_3Cr_1$/zeolite catalysts, including a $Zn_3Cr_1$/SSZ-13 catalyst.

In some embodiments, the zeolite catalyst comprises a zeolite with Zn oxide nanoparticles, M oxide nanoparticles, and $ZnMO_x$ oxide nanoparticles disposed on the zeolite. In some embodiments, the Zn oxide nanoparticles, the M oxide nanoparticles, and the $ZnMO_x$ oxide nanoparticles have particle sizes of about 0.5 nanometers to 1 nanometer.

In some embodiments, the zeolite catalyst comprises a zeolite with $ZnMO_x$ oxide nanoparticles disposed on the zeolite. In some embodiments, the $ZnMO_x$ oxide nanoparticles have particle sizes of about 0.5 nanometers to 1 nanometer.

In some embodiments, the surface acidity of the zeolite is neutralized. A process for neutralizing the surface acidity of the zeolite is described further below. In some embodiments, after neutralizing the surface acidity of the zeolite, surfaces of the zeolite have $Na^+$ ions attached thereto.

In some embodiments, the process 500 further comprises dehydrating the zeolite prior to block 500. In some embodiments, the dehydrating comprises heating the zeolite to about 60° C. to 180° C., or about 120° C., for about 1.5 hours to 4.5 hours, or about 3 hours, while under a vacuum.

In some embodiments, the process 500 further comprises neutralizing the surface acidity of the zeolite after block 515. For example, some zeolites that are used in the embodiments described herein are proton-type zeolites that have a high surface acidity. Proton-type zeolites include HSSZ-13 zeolite, HZSM-5 zeolite, H-ZSM-11 zeolite, H-ZSM-22 zeolite, H-ZSM-23 zeolite, and Beta zeolite. In some embodiments, neutralizing the surface acidity of the zeolite comprises $Na^+$-neutralizing the zeolite. In some embodiments, $Na^+$-neutralizing the zeolite comprising dispersing the mixture in deionized water to form a suspension, adding a sodium bicarbonate solution to the suspension so that the suspension has a pH of about 7, and removing the mixture from the suspension.

Figure 7:
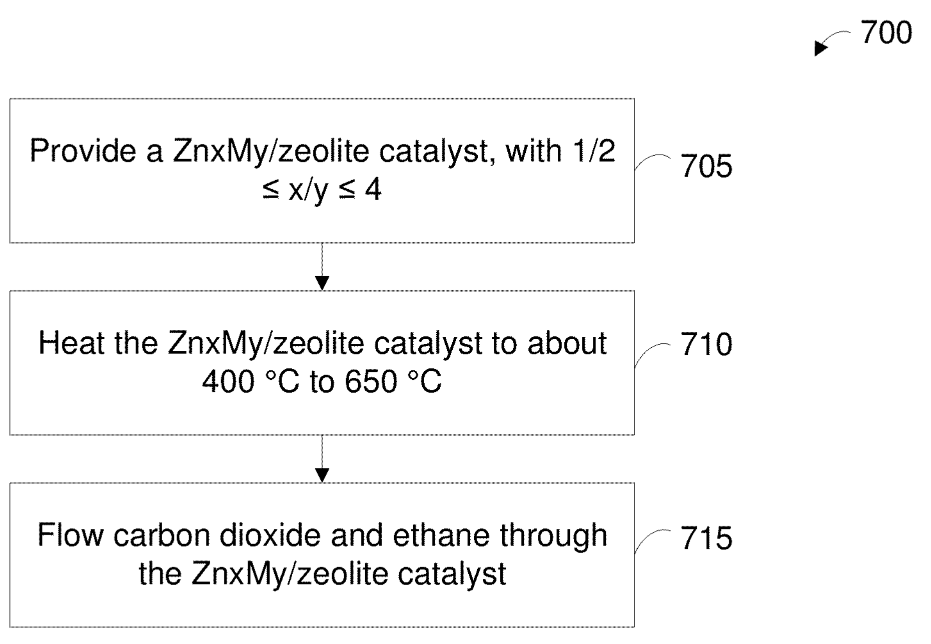
FIG. 7 shows an example of a flow diagram illustrating a method of co-conversion of ethane to $CO_2$ using a Zn-metal oxide/zeolite catalyst.

FIG. 7 shows an example of a flow diagram illustrating a method of co-conversion of ethane to $CO_2$ using a Zn-metal oxide/zeolite catalyst. Starting at block 705 of the process 700 shown in FIG. 7, a ZnxMy/zeolite catalyst is provided, with $\frac{1}{2} \le x/y \le 4$, with M being a metal from a group Cr, Mo, and W, with Zn being an oxide, with M being an oxide, and with at least some $ZnMO_x$ oxides.

The process 700 may be performed with any of the zeolite catalysts described herein. For example, in some embodiments, the zeolite is a zeolite from a group HSSZ-13 zeolite, NaSSZ-13 zeolite, HZSM-5 zeolite, NaZSM-5 zeolite, H-ZSM-11 zeolite, H-ZSM-22 zeolite, H-ZSM-23 zeolite, ZSM-35 zeolite, Beta zeolite, SAPO-11 zeolite, and SAPO-34 zeolite. In some embodiments, the zeolite catalyst is a $Zn_3M_1$/zeolite catalyst. In some embodiments, the zeolite catalyst is a $Zn_3Cr_1$/SSZ-13 catalyst.

At block 710, the ZnxMy/zeolite catalyst is heated to about 400° C. to 650° C. In some embodiments, the zeolite catalyst is heated in a furnace.

At block 715, carbon dioxide and ethane are flowed through the ZnxMy/zeolite catalyst, generating carbon monoxide and ethylene. In some embodiments, the ratio of carbon dioxide to ethylene is about 5 to 1 to about 1 to 1.

The following examples are intended to be examples of the embodiments disclosed herein, and are not intended to be limiting.

Example—Materials Synthesis $Zn_xCr_y$/SSZ-13 (x=1, y=0; x/y=½, 1, 2, 3, and 4; x=0, y=1) catalysts were prepared by a dry-deposition method. The total amount of Zn and Cr in all catalysts was set at 0.8 mmol per 1 gram (g) of support materials.

In a typical synthesis, the SSZ-13 zeolite support was pretreated in a vacuum at 120° C. for 3 h to remove moisture. A stoichiometric amount of Zinc (II) acetate and/or chromium (III) acetate hydroxide (Zn+Cr=0.8 mmol) was mixed with 1 g of SSZ-13 zeolites using an analog vortex mixer. The resulting solid mixtures were ground in glove box for 20 minutes. Subsequently, the samples were heated in flowing $N_2$ (100 mL/min) at 550° C. for 3 hours at a ramping rate of 2° C./min and subsequently in flowing air (100 ml/min) for another 3 hours. Both $N_2$ and air were purified by moisture trap. Afterward, the resulting materials were pretreated through $Na^+$-neutralization. Typically, the sample was firstly dispersed in deionized water and then dropwise addition of sodium bicarbonate solution (0.01 M, pH=8) was performed until the solution reached a pH of 7. The slurry was then collected and dried at 110° C. overnight. The samples were finally calcined in static air at 500° C. for 2 hours with a ramping rate of 2° C./min. The final products were stored in an $N_2$ box. The control samples of $Zn_xCr$/SSZ-13 (x=½, 1, and 3) were synthesized using a co-precipitation (CP) method, followed by $Na^+$ neutralization.

Example—Catalytic Performance Experiments

Catalytic performance experiments for the iso-stoichiometric co-conversion of ethane and $CO_2$ (ICEC) were conducted in a continuous fix-bed reactor in the temperature range of 400° C. to 550° C. and under ambient pressure using an electric furnace with temperature controlled by a K-type thermocouple. In a typical catalytic measurement, a total of 200 mg catalyst diluted with 800 mg sand was loaded into the middle of the reactor plugged by quartz wool on two sides. Before the catalytic test, the catalyst bed was pretreated under a flow of Argon (25 sccm) at 550° C. for 1 hour with a ramping rate of 10° C. from room temperature. Afterward, the reactant mixtures including 5% $CO_2$ and 5% $C_2H_6$ balanced with argon were introduced at a total flow rate of 25 sccm. Argon was used as an internal standard. The reaction products were analyzed with a gas chromatograph equipped with a thermal conductivity detector (TCD) and a flame ionization detector (FID).

To better reveal the reaction kinetics, apparent activation barriers were determined in the temperature range of 400° C. to 475° C. (the conversions of $CO_2$ and $C_2H_6$ are less than 10%). The carbon and oxygen balances were within 100±2% for all tests. The conversions of $CO_2$ and $C_2H_6$, $C_2H_4$ selectivity, utilization of converted $CO_2$ ($U_{CO_2}$), $C_2H_4$ yield, the turnover frequency (TOF) of $C_2H_4$ formation, and the space time yield (STY) of $C_2H_4$ formation were calculated as follows (where n is the molar flow of substance (mol/min), $n_{Zn+Cr}$ is the total molar loading of Zn and/or Cr, $M_{C_2H_4}$ is the molecular weight of $C_2H_4$ (28 g/mol), and $m_{cat}$ is the catalyst mass (kg)):

$$CO_2\text{ conversion }(\%) = \frac{n_{CO_2 input} - n_{CO_2 output}}{n_{CO_2 input}} \times 100\% \quad (1)$$

$$C_2H_6\text{ conversion }(\%) = \frac{n_{C_2H_6 input} - n_{C_2H_6 output}}{n_{C_2H_6 input}} \times 100\% \quad (2)$$

$$C_2H_4\text{ selectivity }(\%) = \frac{n_{C_2H_4 output}}{n_{C_2H_6 input} - n_{C_2H_6 output}} \times 100\% \quad (3)$$

$$U_{CO_2}(\%) = \frac{CO_2\text{ conversion}}{C_2H_6\text{ conversion}} \times 100\% \quad (4)$$

$$C_2H_4\text{ yield }(\%) = C_2H_6\text{ conversion} \times C_2H_4\text{ selectivity} \quad (5)$$

$$TOF = \frac{n_{C_2H_4 output} \times 60}{n_{Zn+Cr}} \quad (6)$$

$$STY = \frac{n_{C_2H_4 output} \times M_{C_2H_4} \times 60}{1000 \times m_{cat}} \quad (7)$$

It is noted that calculations of $U_{CO_2}$ were also calibrated and examined by the equation:

$$U_{CO_2}(\%) = \frac{n_{CO\ output}}{n_{C_2H_6 input} \cdot n_{C_2H_6\ output}} \times 100\% \quad (8)$$

Example—Controlling Zn and Cr Coordination Structure

Figures 1A, 1B, 1C, 1D:
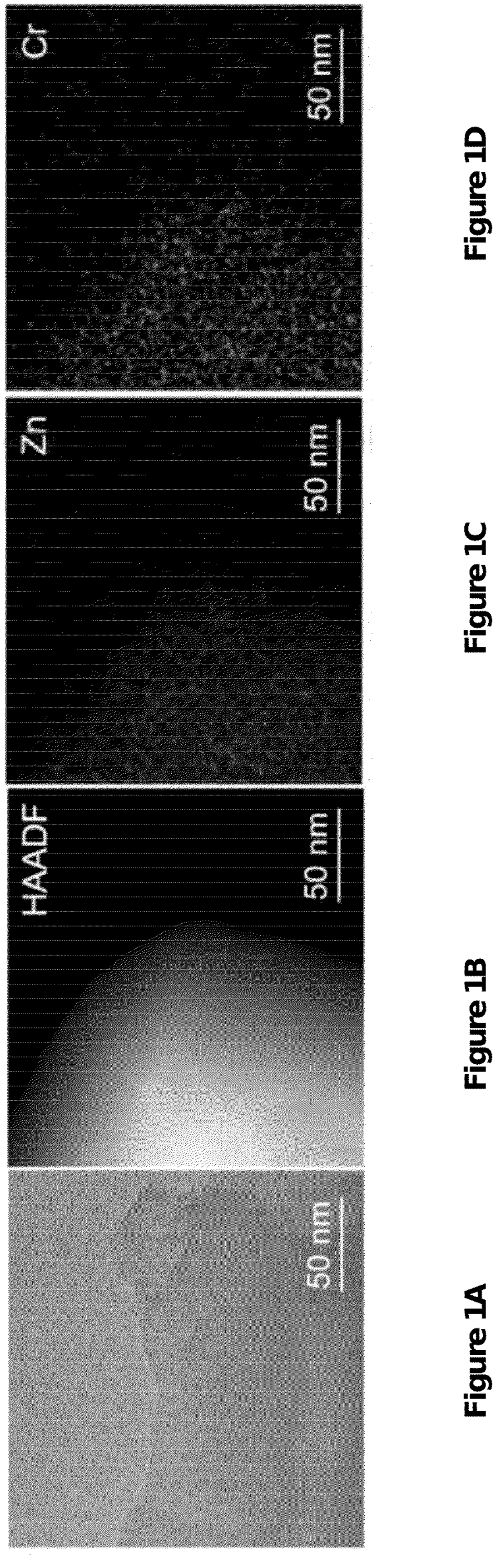
FIG. 1A shows a representative TEM image.
FIG. 1B shows a representative HAADF-STEM image.
FIGS. 1C and 1D show EDS mapping of Zn—O—Cr ABC with Zn/Cr ratio of 3/1.

The catalysts described in the Examples are denoted as $Zn_xCr_y$/SSZ-13, where x/y refers to the ratio of Zn/Cr (x=1, y=0; x/y=½, 1, 2, 3, 4; x=0, y=1). A transmission electron microscopy (TEM) image (FIG. 1A), a scanning TEM (STEM) image, and energy dispersive spectroscopy (EDS) elemental mappings (FIGS. 1C and 1D) show high dispersion of Zn and/or Cr oxide phases, with no observable sintering of oxide nanoparticles.

X-ray diffraction (XRD) results showed the absence of spinel $ZnCr_2O_4$ and zincite ZnO for all dry-deposition synthesized catalysts. $Cr_2O_3$ phases with R3c space group were only observed in Cr/SSZ-13 and $Zn_1Cr_2$/SSZ-13. The control catalysts with same amount Zn and Cr precursors were prepared via a co-precipitation method (CP), followed by $Na^+$ neutralization. $ZnCrO_x$ nanoparticles are observed in CP-synthesized catalysts. Aa phase transition from spinel $ZnCr_2O_4$ to ZnO was seen with CP-synthesized catalysts with Zn/Cr ratios varying from 1/2 to 3/1.

Figures 1E, 1F, 1G:
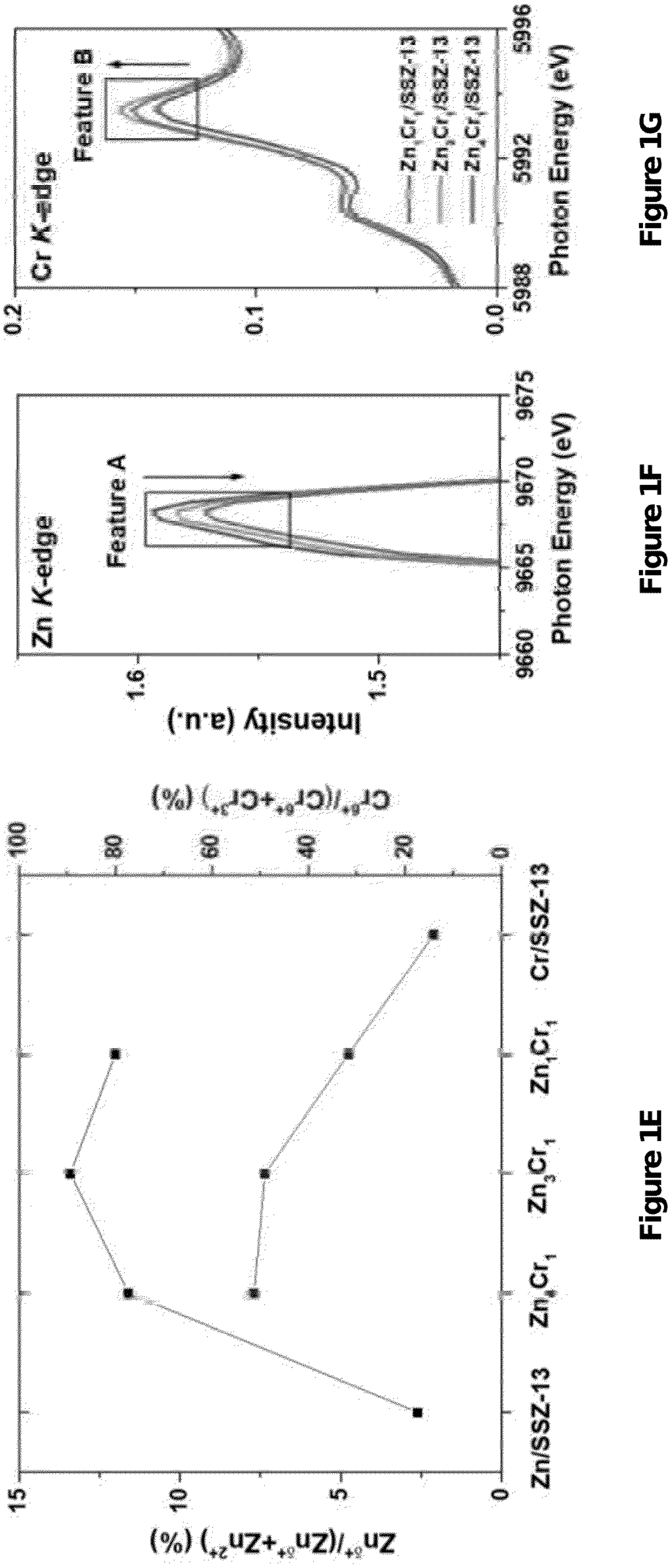
FIG. 1E shows the proportion of $Zn^{\delta+}$ ($0<\delta<2$) (left) and $Cr^{6+}$ (right) with varying Zn/Cr ratios (Results derived from Auger spectra of Zn LMM and Cr $2p_{3/2}$ XPS spectra).
FIGS. 1F and 1G show enlarged electron transition features in Zn and Cr K-edge XANES spectra.

The formation of $Zn^{\delta+}$ ($0<\delta<2$) was confirmed through Auger spectra of Zn LMM. Subpeaks at 987.5 and 990.0 eV in Auger spectra of Zn LMM were assigned to the $Zn^{2+}$ and $Zn^{\delta+}$ ($0<\delta<2$), respectively; the subpeaks at ~576 and ~580 eV in Cr $2p_{3/2}$ XPS were assigned to the $Cr^{3+}$ and $Cr^{6+}$, respectively. FIG. 1E shows the proportion of $Zn^{\delta+}$ ($0<\delta<2$) and $Cr^{6+}$ relative to the total amount of ($Zn^{\delta+}+Zn^{2+}$) and ($Cr^{6+}+Cr^{3+}$) in $Zn_xCr_y$/SSZ-13 catalysts, respectively. These proportions vary with Zn/Cr ratios, with the highest $Zn^{\delta+}$ ($0<\delta<2$) proportion generated at Zn/Cr ratio of 3/1 and the highest $Cr^{6+}$ proportions produced at Zn/Cr ratios of 3/1 and 4/1. It is hypothesized that the proximal electronic interactions between Zn and Cr could modify their respective oxidation states. This is consistent with the Zn $L_3$-edge X-ray absorption near-edge structure (XANES) spectra analyses, which suggests a decrease in the oxidation state of Zn in Zn Cr/SSZ-13 catalysts compared to pure Zn/SSZ-13 catalyst. The $Zn^{\delta+}$ and $Cr^{6+}$ content in the CP-synthesized $Zn_3Cr_1$/SSZ-13 catalyst was similar to those of pure Zn/SSZ-13 and Cr—SSZ-13 catalysts, respectively.

XANES spectra and extended X-ray absorption fine structure (EXAFS) spectra were used to study coordination structures of Zn and Cr sites. As shown in FIGS. 1F and 1G, the electron transition from Zn 1s to Zn 4p unoccupied orbitals (Feature A) is revealed in Zn K-edge XANES spectra; and Cr K-edge XANES spectra exhibits the peak of electron transition from Cr 1s to Cr 3d-O 2p unoccupied orbitals (Feature B). As the Zn/Cr ratio increases from 1/1 to 4/1 in $Zn_xCr_y$/SSZ-13 catalysts, the intensity of feature A decreases, suggesting electron occupation in Zn 4p unoccupied orbitals, while the intensity of feature B increases, which suggests electrons transfer out of Cr 3d-O 2p orbitals near the conduction band minimum. It is hypothesized that a link between these observations, that electronic charge transfers from Cr 3d-O 2p character in the conduction band to Zn 4p, due to a strong Zn—Cr interaction. Thus, the charge transfer decreases the oxidative state of $Zn^{2+}$ to $Zn^{\delta+}$ ($0<\delta<2$), which is consistent with XPS and Auger results (FIG. 1E).

Figure 1I:
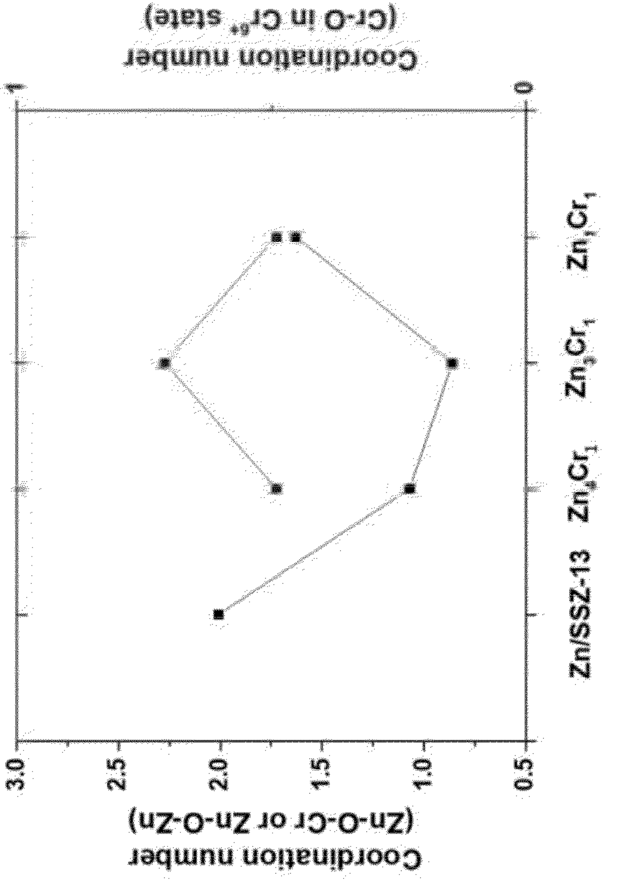
FIG. 1I shows the coordination number (CN) of Zn—O—Cr(Zn) and Cr—O in $Cr^{6+}$ state in Zn—O—Cr ABCs with varying Zn/Cr ratios.
Figure 1H:
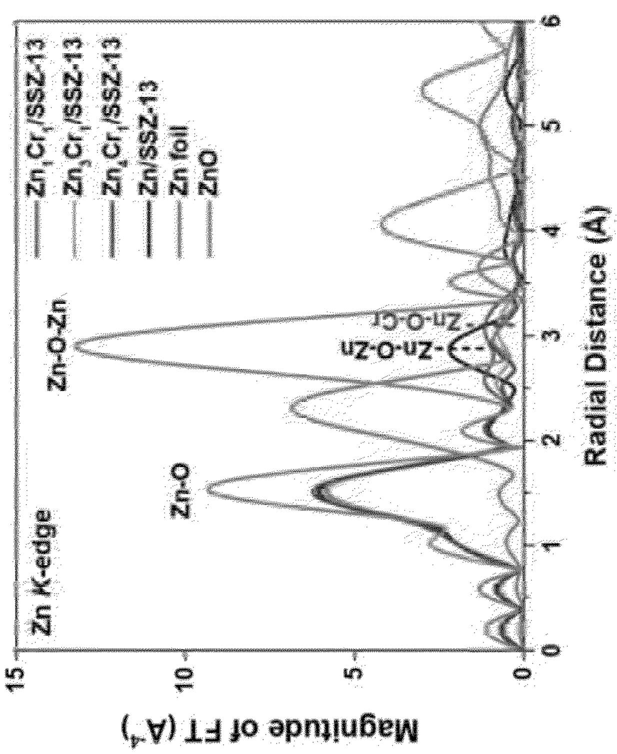
FIG. 1H shows $k^3$-weighted Fourier-transformed extended X-ray absorption fine structure (FT-EXAFS) spectra (Zn K-edge) of Zn—O—Cr ABCs with varying Zn/Cr ratios, with Zn foil and ZnO as references.

In FIG. 1H, the scattering peaks at 1.50 Å were assigned to Zn—O coordination in the first shell. The pure Zn/SSZ-13 and $Zn_xCr_y$/SSZ-13 catalysts exhibited a significantly lower intensity for this Zn—O scattering peak than the ZnO reference, suggesting a higher degree of crystal disorder. The scattering peaks at ~2.85 Å were assigned to Zn—O—Zn coordination in the second shell. Compared to Zn/SSZ-13 and the ZnO reference, $Zn_1Cr_1$/SSZ-13 and $Zn_3Cr_1$/SSZ-13 exhibited no peak for Zn—O—Zn coordination. Instead, a new peak at ~3.08 Å should be attributed to the Zn—O—Cr bond. Differently, the $Zn_4Cr_1$/SSZ-13 catalyst has both Zn—O—Cr and Zn—O—Zn bonds.

Cr K-edge Fourier transformed EXAFS (FT-EXAFS) spectra of Cr-containing catalysts showed Cr—O scattering peaks located at 1.51 Å, which is similar to standard peak of Cr—O scattering 1.50 Å in $Cr^{III}_2O_3$; but as Zn/Cr ratio increased to 3/1 and 4/1, a visible shoulder peak corresponding to standard peak of Cr—O scattering at 1.20 Å in $K_2Cr^{VI}_2O_7$ appeared, indicating that $Zn_3Cr_1$/SSZ-13 and $Zn_4Cr_1$/SSZ-13 catalysts have two types of Cr—O coordination.

$Zn_xCr_y$/SSZ-13 catalyst (x/y=1, 3, 4) catalysts showed Zn—O—Cr coordination with a bond distance ~3.4 Å in phase-corrected space, which corresponds to the emergent peak at ~3.08 Å in FIG. 1H. These results provide evidence for the formation of a $Zn^{\delta+}$—O—$Cr^{6+}$ structure in $Zn_xCr_y$/SSZ-13. Note that $Zn_xCr_y$/SSZ-13 catalysts also exhibited lower coordination numbers (CN) for Zn—O and Zn—O—Cr compared to the pure Zn/SSZ-13 catalyst (FIG. 1I), which results from Cr colocalization. Especially for the $Zn_3Cr_1$/SSZ-13 and $Zn_4Cr_1$/SSZ-13 catalysts, the CNs of Zn—O and Zn—O—Cr are 3.94 and 0.86, and 3.77 and 1.07, respectively. $Zn_3Cr_1$/SSZ-13 has the highest CN for the Cr—O bond in hexavalent ($Cr^{6+}$) states. These results confirm the formation of hetero binuclear $Zn^{\delta+}$—O—$Cr^{6+}$ sites, and $Zn_3Cr_1$/SSZ-13 exhibits the highest population of the $Zn^{\delta+}$—O—$Cr^{6+}$ site.

Example—Catalytic Performance of Zn—O—Cr ABC for ICEC

Figures 2B, 2C, 2D, 2E:
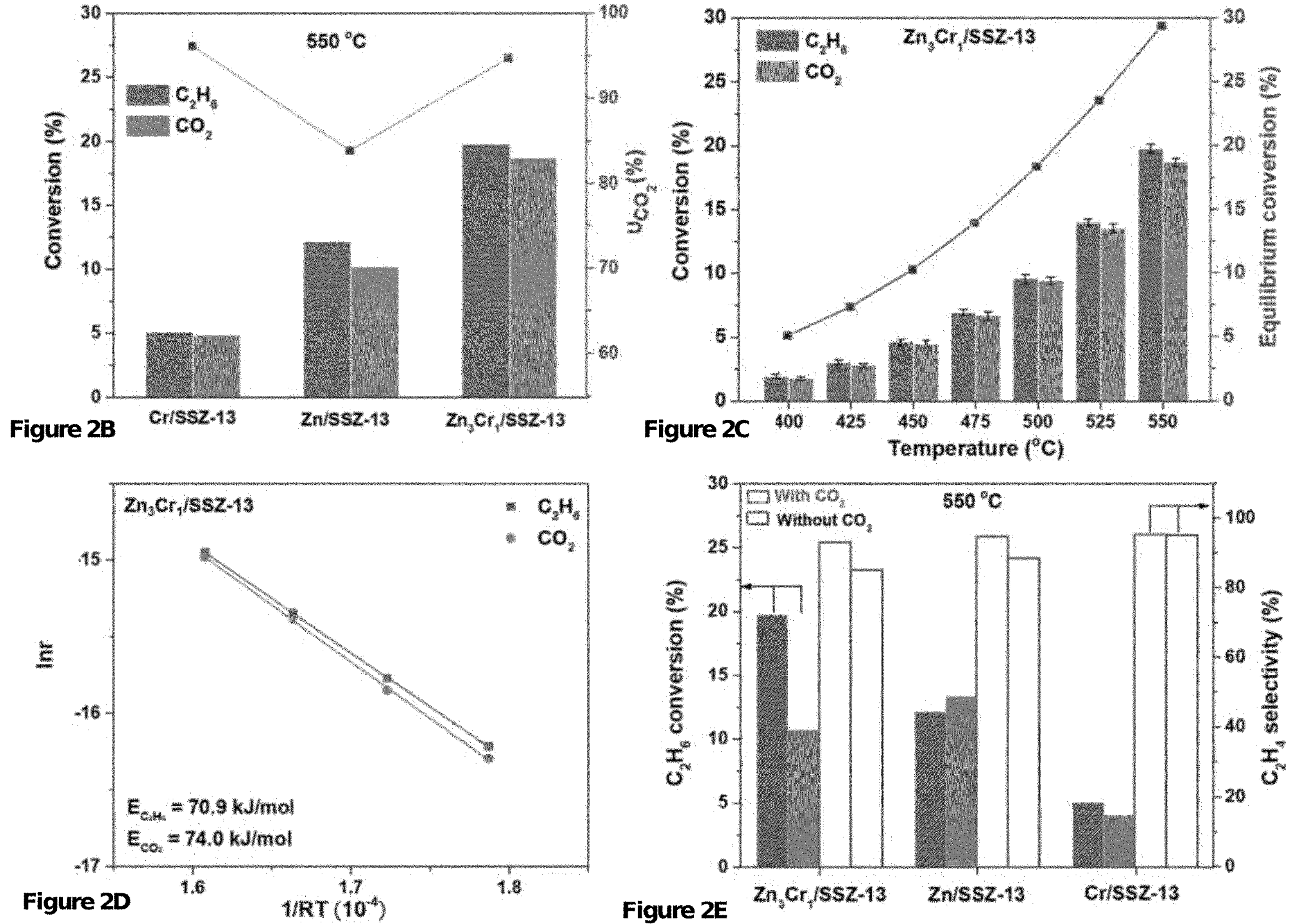
FIG. 2B shows $C_2H_6$ and $CO_2$ conversion, utilization of converted $CO_2$ ($U_{CO_2}$) of Cr/SSZ-13, Zn/SSZ-13, and $Zn_3Cr_1$/SSZ-13 catalysts in ICEC at 550° C.
FIG. 2C shows the reaction temperature dependent performance of $Zn_3Cr_1$/SSZ-13 catalyst.
FIG. 2D shows Arrhenius plots of $Zn_3Cr_1$/SSZ-13 catalyst (obtained when both $C_2H_6$ and $CO_2$ conversions are <10%).
FIG. 2E shows $C_2H_6$ conversion and $C_2H_4$ selectivity over $Zn_3Cr_1$/SSZ-13, Zn/SSZ-13, and Cr/SSZ-13 with (black columns) and without (gray columns) $CO_2$ at 550° C.

FIGS. 2A and 2B show the ICEC catalytic performance of Zn—O—Cr ABCs under the reaction conditions of weight hourly space velocity (WHSV) of 7500 mL $g_{cat}^{-1}$ $h^{-1}$ and a $CO_2$/ethane ratio of 1 at 550° C. The $Zn_3Cr_1$/SSZ-13 ABC catalyst displayed the best performance among all of the tested catalysts, with the highest $C_2H_6$ conversion (19.8%), $CO_2$ conversion (18.7%), and turnover frequency (TOF) of $C_2H_4$ formation (0.77 mol $mol_{Zn+Cr}^{-1}$ $h^{-1}$), as well as excellent $C_2H_4$ selectivity (93.0%) and $U_{CO_2}$ (94.4%).

Previous studies have mainly focused on achieving high ethane conversion and ethylene selectivity in the co-conversion of ethane and $CO_2$ by co-feeding excess $CO_2$ at $CO_2$/ethane ratios of 2 to 6. In the ICEC process the $C_2H_4$ selectivity and $U_{CO_2}$ are two important factors for evaluating the success of the catalyst development. Utilization of converted $CO_2$ ($U_{CO_2}$) is defined as the ratio of $CO_2$ conversion to ethane conversion on an iso-stoichiometric basis.

Compared with previous studies, the $Zn_3Cr_1$/SSZ-13 catalyst displays the highest space-time yield (STY) of $C_2H_4$ formation (0.086 kg $h^{-1}$ $kg_{cat}^{-1}$) and the highest $U_{CO_2}$ at 550° C., which clearly shows the superiority of Zn—O—Cr ABCs. Further, FIG. 2C shows $C_2H_4$ selectivity can achieve 100% and $U_{CO_2}$ is 99.0% under the reaction temperature of 500° C., with ethane conversion of 9.6% and $CO_2$ conversion of 9.5%. These results further demonstrate the advantage of Zn—O—Cr ABCs suitable for ICEC. In ICEC, the reaction system includes the reactants' (ethane and $CO_2$) adsorption, activation, reaction, and products' (ethylene, CO, and $H_2O$) formation, and desorption. The apparent activation energies (Ea) for ethane conversion and $CO_2$ conversion are key to evaluating the rate matching of both reactions. FIG. 2D shows similar Ea (results were calculated based on FIG. 2C) for ethane dehydrogenation (70.9 KJ/mol) and $CO_2$ hydrogenation (74.0 KJ/mol). This further demonstrates the feasibility and success of the Zn—O—Cr ABCs concept for desired ICEC catalyst development.

FIG. 2A shows that there is a correlation between the proportion of $Zn^{\delta+}$—O—$Cr^{6+}$ sites and ICEC performance. Pure Cr/SSZ-13 catalyst had slightly higher ethylene selectivity (95.4%) and higher $U_{CO_2}$ (96.0%) than $Zn_3Cr_1$/SSZ-13 catalyst, but had the lowest $C_2H_6$ conversion (5.1%), $CO_2$ conversion (4.9%), and TOF of $C_2H_4$ formation (0.20 mol $mol_{Zn+Cr}^{-1}$ $h^{-1}$). Increasing Zn content in Zn—O—Cr ABCs, with Zn/Cr ratios from 1/2 to 3/1, had little effect on ethylene selectivity and $U_{CO_2}$. Instead, increased Zn content promoted higher conversion of $C_2H_6$ and $CO_2$, and led to increased TOF of ethylene formation. Further increasing the Zn content to Zn/Cr ratio of 4/1 resulted in lower ethane (14.4%) and $CO_2$ (11.7%) conversion, resulting in a much lower $U_{CO_2}$ (81.5%). Pure Zn/SSZ-13 exhibited further decreased $C_2H_6$ (12.1%) and $CO_2$ (10.2%) conversion compared with $Zn_4Cr_1$/SSZ-13. Therefore, it is hypothesized that the $Zn^{\delta+}$ in the binuclear site of $Zn^{\delta+}$—O—$Cr^{6+}$ is the primary active site for $C_2H_6$ dehydrogenation.

Interestingly, the $Zn^{\delta+}$ proportion also showed a correlation with $CO_2$ conversion, which indicates that the $Zn^{\delta+}$ sites are also involved in $CO_2$ adsorption, activation, or reaction. In previous studies, binuclear Zn—O—Zn catalysts have been reported to have a high activity in ethane or propane dehydrogenation, but lack the capacity of efficient $CO_2$ activation, leading to insufficient $CO_2$ utilization. In this study, the $Zn_3Cr_1$/SSZ-13 ABC with the highest amount of $Zn^{\delta+}$—O—$Cr^{6+}$ sites displayed ~1.5 and ~4-fold higher ethane dehydrogenation and $CO_2$ conversion performance than pure Zn and Cr catalysts, respectively (FIG. 2B), which indicates the $Cr^{6+}$ site of $Zn^{\delta+}$—O—$Cr^{6+}$ is also involved in the activation and reaction of $C_2H_6$ and $CO_2$. From the above analyses, it is concluded that the unique performance of Zn—O—Cr ABCs for ICEC is due to the atomic synergies within the $Zn^{\delta+}$—O—$Cr^{6+}$ site.

To study the atomic synergies between $Zn^{\delta+}$—O—$Cr^{6+}$ site in ICEC, $C_2H_6$ dehydrogenation performance of $Zn_3Cr_1$/SSZ-13 with pure Zn/SSZ-13 and Cr/SSZ-13 catalysts in the presence and absence of $CO_2$ were compared. As shown in FIG. 2E, the $CO_2$ co-feeding significantly improved $C_2H_6$ conversion (19.8% vs. 10.7%) and $C_2H_4$ selectivity (93.0% vs. 85.0%) for $Zn_3Cr_1$/SSZ-13, with a high $U_{CO_2}$ up to 94.4%. In contrast, for Zn/SSZ-13, $CO_2$ addition failed to enhance its $C_2H_6$ conversion (12.1% vs. 13.3%) but resulted in an increase in $C_2H_4$ selectivity (94.6% vs. 86.0%). The higher $C_2H_4$ selectivity is due to competitive adsorption of $CO_2$ over $C_2H_6$, preventing the ethane cracking reaction, which has been reported previously. Compared with Zn/SSZ-13, the improved $C_2H_6$ conversion of the $Zn_3Cr_1$/SSZ-13 catalyst is due to the generation of $Zn^{\delta+}$ in $Zn^{\delta+}$—O—$Cr^{6+}$. For the Cr/SSZ-13 catalyst, $CO_2$ introduction resulted in a higher $C_2H_6$ conversion (5.1% vs 4.0%) with a high $U_{CO_2}$ of 96%, but it did not change the $C_2H_4$ selectivity (95.4% vs 95.1%). Cr-based catalysts have been reported to catalyze $CO_2$ and ethane conversion through the redox (or MvK) mechanism. $CO_2$ introduction could favor lattice oxygen replenishment to regenerate highly reactive $Cr^{6+}$ species and shift the reaction equilibrium of $C_2H_6$ dehydrogenation, thus leading to a higher activity. These results indicate that a reaction synergy between ethane and $CO_2$ conversions could occur at the atomically synergistic $Zn^{\delta+}$—O—$Cr^{6+}$ site.

To further validate the Zn—O—Cr ABCs, the performance of $Zn_3Cr_1$/SSZ-13 prepared by the dry-deposition method with the catalyst synthesized by the traditional co-precipitation (CP) method were compared. The dry-deposition synthesized $Zn_3Cr_1$/SSZ-13 catalyst exhibited >4-fold higher ethane conversion (19.8% vs 4.5%) and higher $U_{CO_2}$ (94.4% vs 83.2%). The CP-synthesized $Zn_3Cr_1$/SSZ-13 catalyst contained large Zn/Cr oxide particles and separate $ZnCr_2O_4$ and ZnO phases, resulting in loss of the atomic synergies of the $Zn^{\delta+}$—O—$Cr^{6+}$ site, which is thought to correlate with its poor performance. The stability and regeneration ability of the $Zn_3Cr_1$/SSZ-13 ABC catalyst was also studied. The ethylene selectivity and $U_{CO_2}$ remained nearly 100% during a total of 150 h in 3 cycles. The decayed conversion of ethane and $CO_2$ can be totally regenerated by oxidative treatment in air at 500° C. This excellent durability and regeneration ability demonstrates the structural stability of $Zn^{\delta+}$—O—$Cr^{6+}$ site.

Figures 3A, 3B, 3C:
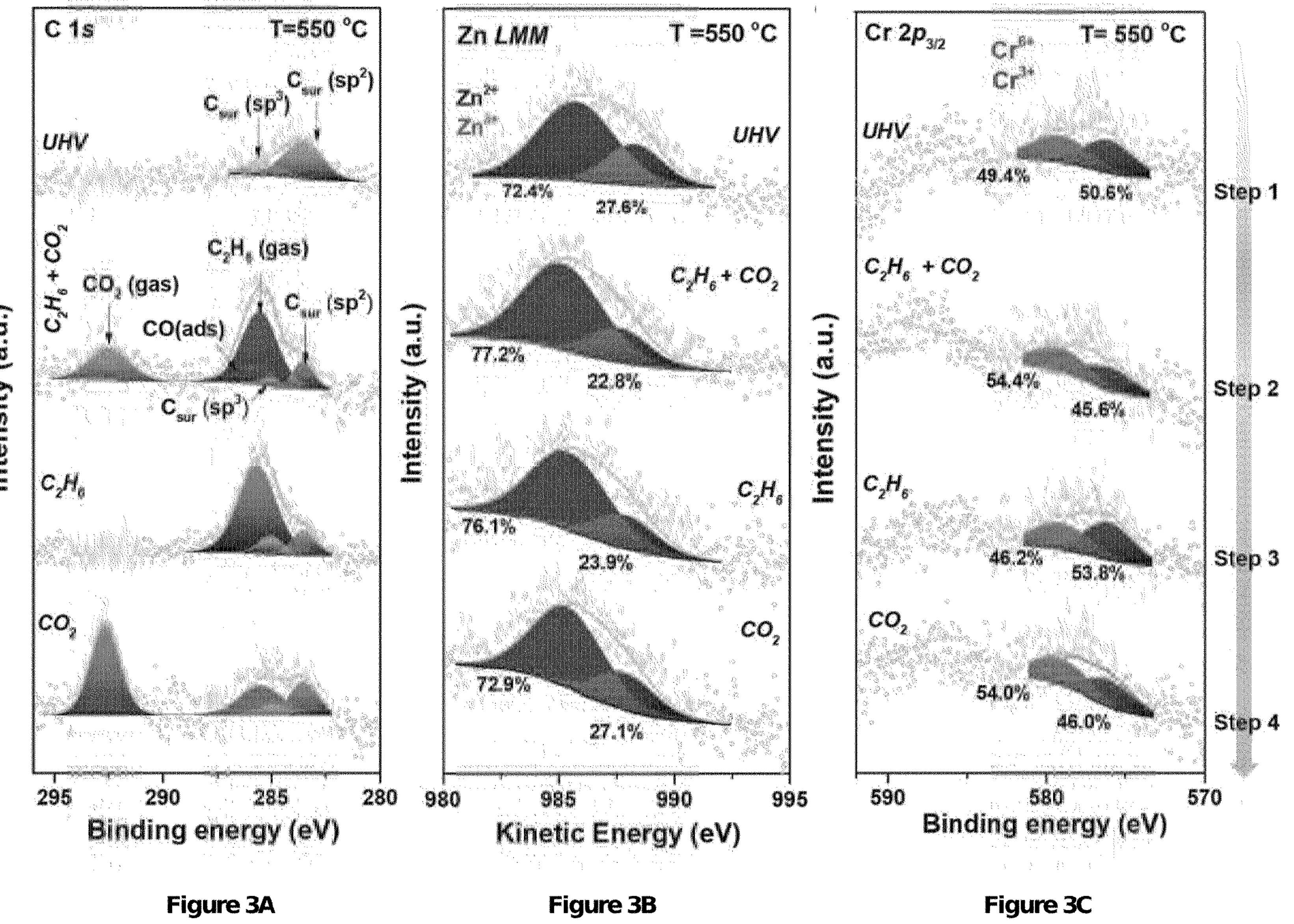
FIGS. 3A-3C show in situ ambient pressure X-ray photoelectron spectroscopy (APXPS)

Example—Electronic Structure of Binuclear $Zn^{\delta+}$—O—$Cr^{6+}$ Sites During the Reaction In situ ambient pressure X-ray photoelectron spectroscopy (APXPS) was used to examine the electronic structure of binuclear $Zn^{\delta+}$—O—$Cr^{6+}$ sites and study the atomic synergies between $Zn^{\delta+}$ and $Cr^{6+}$ sites in ICEC. FIGS. 3A-3C show ambient pressure spectra indicating C 1s binding energies, Zn LMM Auger kinetic energies, and Cr $2p_{3/2}$ binding energies.

Step 1: $Zn_3Cr_1$/SSZ-13 was first tested under 550° C. in an ultra-high vacuum (UHV). The temperature of 550° C. was used to match the reaction temperature used in the experiments used to generate FIGS. 2A-2E. 2. In Auger spectra of Zn LMM (FIG. 3B), both $Zn^{2+}$ and $Zn^{\delta+}$ species were detected with a percentage distribution of 72.4% and 27.6%, respectively. As shown in FIG. 3C, $Cr^{3+}$ and $Cr^{6+}$ were detected with a proportion of 50.6% and 49.4%, respectively.

Figure 3D:
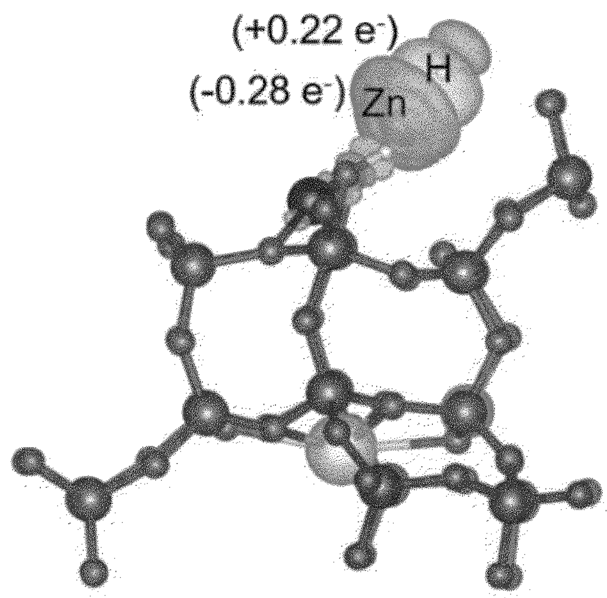
FIG. 3D shows a schematic illustration of electron transfer from Zn to H after the $2^{nd}$ C—H bond scission in ethane, where electron accumulation ($\Delta\rho=+1\times10^{-3}$ e $bohr^{-3}$) and depletion ($\Delta\rho=-1\times10^{-3}$ e $bohr^{-3}$) and ($\Delta\rho=-1\times10^{-3}$ e $bohr^{-3}$) being represented.

Step 2: The $Zn_3Cr_1$/SSZ-13 was subjected to simulated reaction conditions of ICEC by co-feeding 50 mTorr $C_2H_6$ and 50 mTorr $CO_2$ under 550° C. The signals of gaseous $C_2H_6$ and $CO_2$ were detected as shown in FIG. 3A. Notably, adsorbed CO species ($CO_{ads}$) at 285.5 eV were observed, which indicates the ICEC reaction occurred. Under the reaction conditions, the proportion of $Zn^{\delta+}$ decreased (from 27.6% to 22.8%) and $Cr^{6+}$ ratio increased (from 49.4% to 54.4%). DFT calculations (FIG. 3D) indicate that the oxidation from $Zn^{\delta+}$ to $Zn^{2+}$ is due to the formation of Zn—$H^{\delta-}$ hydride during the ethane dehydrogenation, with more negative charge accumulated on $H^{\delta-}$. The oxidation of $Cr^{3+}$ to $Cr^{6+}$ may result from lattice oxygen replenishment via $CO_2$ dissociation. These results indicate both $Zn^{\delta+}$ and $Cr^{6+}$ were involved in the ICEC reaction.

Steps 3 and 4: Steps 3 and 4 were designed to help to understand the role of individual $Zn^{\delta+}$ or $Cr^{6+}$ in ICEC. When feeding 100 mTorr $C_2H_6$ (without $CO_2$) in step 3 (FIGS. 3A and 3B), the signals of $CO_2$ and $CO_{ads}$ species disappeared, which indicates that only ethane dehydrogenation could occur. The proportions of $Zn^{2+}$ and $Zn^{\delta+}$ remained similar to the case of co-feeding $C_2H_6$ and $CO_2$ in step 2, indicating the formation of Zn—$H^{\delta-}$ hydride during the ethane dehydrogenation. Notice that the proportions of $Zn^{\delta+}$ and $Zn^{2+}$ are comparable between step 1 (UHV) and step 4 (feeding 100 mTorr $CO_2$ without ethane), ruling out the likelihood of oxidation of $Zn^{\delta+}$ to $Zn^{2+}$ by $CO_2$ or its derived intermediates.

Figure 3E:
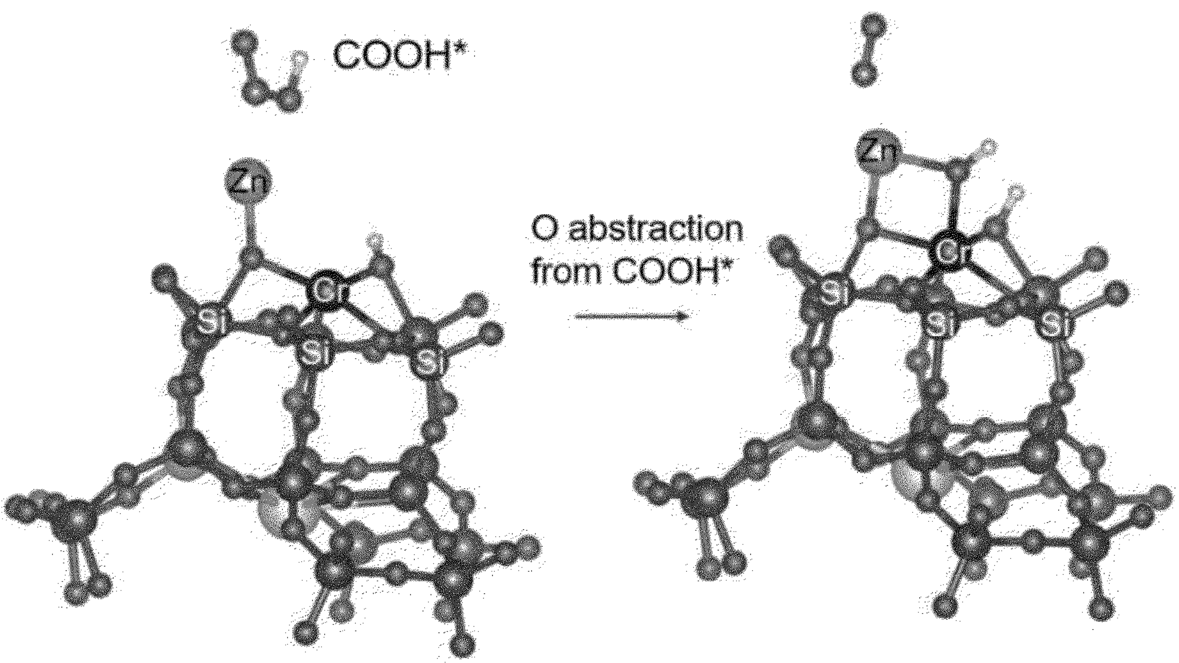
FIG. 3E shows a schematic illustration of the oxidation of Cr in Zn—O—Cr when decomposing COOH* intermediate.

In the case of Cr 2p3/2 XPS spectra (FIG. 3C), the oxidation of $Cr^{3+}$ to $Cr^{6+}$ only occurred when $CO_2$ was fed (steps 2 and 4). Previous studies have demonstrated the oxidation of $Cr^{3+}$ to $Cr^{6+}$ in Cr-based catalysts suffers from sluggish O abstraction from $CO_2$. In the cases shown here, the facile reoxidation of $Cr^{3+}$ to $Cr^{6+}$ may be due to the possibility that nearby $Zn^{\delta+}$ facilitate the $CO_2$ activation to enable easier O abstraction. The $CO_{ads}$ species at 285.5 eV were detected in the presence/co-presence of $CO_2$ in the C 1s spectra (FIG. 3A, steps 2 and 4), which further demonstrates facile $CO_2$ dissociation over the $Zn^{\delta+}$—O—$Cr^{6+}$ site. The DFT calculation (FIG. 3E) indicates that the intermediate of $CO_2$ activation is carboxyl (COOH*). The decomposition of COOH* requires the participation of the Cr site through the formation of a new Cr—O bond (d(Cr—O) =2.08 Å), which will maintain its high oxidation state. In summary, the APXPS results show that binuclear $Zn^{\delta+}$—O—$Cr^{6+}$ sites serve as atomically synergistic sites for ICEC.

Example—Atomically Synergistic Mechanism

Figure 4A:
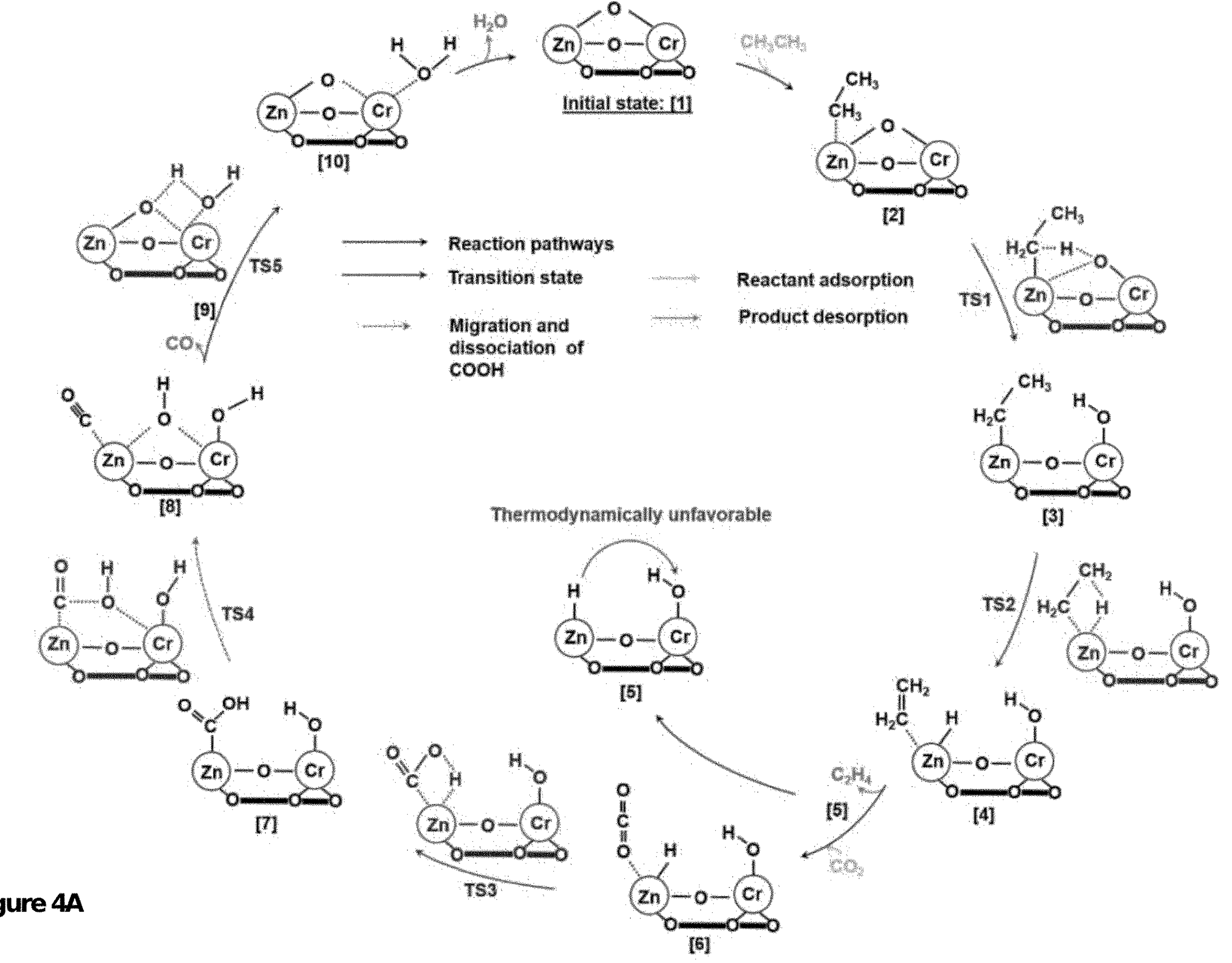
FIGS. 4A and 4B show examples of illustrations of the atomically synergistic mechanism of ICEC over binuclear Zn—O—Cr sites.

Atomically synergistic mechanisms for ICEC on binuclear Zn—O—Cr sites were developed. FIG. 4A shows that the catalytic cycle is initiated by $C_2H_6$ adsorption on Zn ([1]→[2]), then heterolytic cleavage of the first C—H bond (0.93 eV) by breaking a Zn—O—Cr bond to form Zn—$CH_2$—$CH_3$ and Cr—OH ([2]→[3]), followed by a homolytic scission of the β-C—H bond (2.11 eV) ([3]→[4]), and finally, $C_2H_4$ desorption and Zn—$H^{\delta-}$ hydride formation ([4]→[5]). $C_2H_6$ activation at the Cr of Zn—O—Cr sites has higher energy barriers for the first C—H cleavage (1.78 eV vs 0.93 eV) and β-C—H bond dissociation (>3.0 eV vs 2.11 eV), leading to a kinetically unfavorable pathway. In the second stage (FIG. 4A), $CO_2$ prefers to adsorb at the Zn—$H^{\delta-}$ site (−0.35 eV) than the Cr site (−0.05 eV) through acid-base interaction ([5]→[6]); $CO_2$ adsorption energy (−0.35 eV) at Zn—$H^{\delta-}$ site is lower than ethane adsorption (−0.17 eV), which will help prevent the $C_2H_6$ cracking reaction. Then Zn—$H^{\delta-}$ enables $CO_2$ hydrogenation ([6]→[7]) to carboxyl (COOH*), followed by CO—OH cleavage and migration of —OH to be shared with Cr ([7]→[8]). Finally, after CO desorption from the Zn site and the formation and desorption of $H_2O$ from the Cr site to replenish lattice oxygen ([8]→[10]), the ICEC catalytic cycle is closed.

Figure 4B:
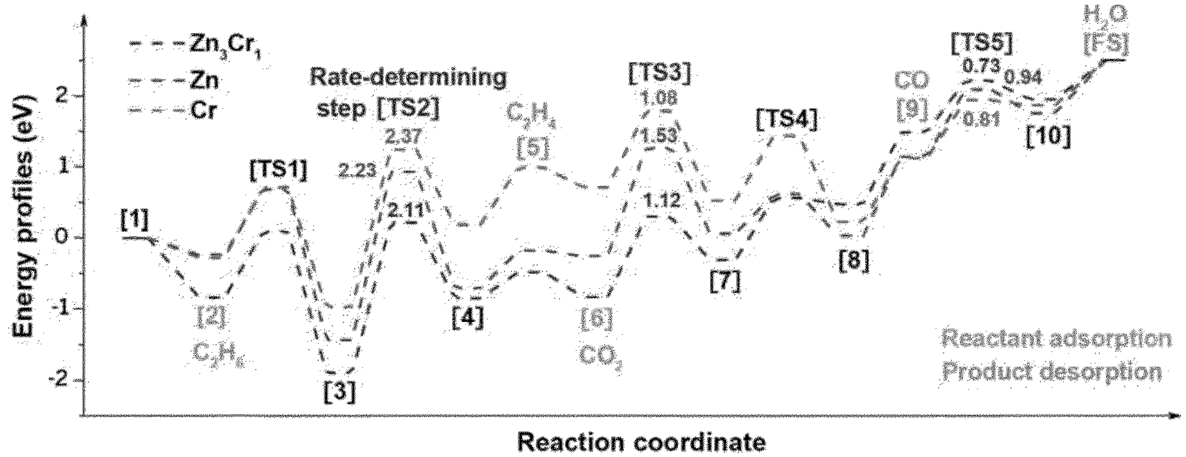

Calculated energy profiles of ICEC over $Zn_3Cr_1$/SSZ-13, Zn/SSZ-13, and Cr/SSZ-13 are shown in FIG. 4B. The rate-determining step of ICEC is the homolytic cleavage of the β-C—H bond in ethane activation [TS2]. $Zn_3Cr_1$/SSZ-13 exhibited a lower activation barrier (2.11 eV) than Zn/SSZ-13 (2.37 eV) and Cr/SSZ-13 (2.23 eV). Moreover, $Zn_3Cr_1$/SSZ-13 also had a lower energy barrier (1.12 eV, 0.73 eV) for $CO_2$ activation [TS3] and $H_2O$ formation [TS5] than Zn/SSZ-13 (1.53 eV, 0.94 eV). This explains the higher $CO_2$ conversion and utilization of $Zn_3Cr_1$/SSZ-13 catalyst than Zn/SSZ-13 catalyst (FIG. 2B). $Zn_3Cr_1$/SSZ-13 exhibited the most favorable energetics of reactants adsorption and products desorption which also helps accelerate catalytic reactions. Therefore, the kinetically and thermodynamically favorable elementary steps in the ICEC catalytic cycle results in the high catalytic performance of $Zn_3Cr_1$/SSZ-13. Its performance in ICEC is due to the atomic synergies between the acidic Zn site and the redox Cr site of ABC.

CONCLUSION

The advantages of an atomically-synergistic binuclear-site catalyst (ABC) synthesized by colocalizing Zn and Cr sites on a zeolite SSZ-13 support (ZnCr/SSZ-13) for the iso-stoichiometric co-conversion of ethane and $CO_2$ (ICEC) reaction has been demonstrated. This ZnCr ABC catalyst exhibited exceptional catalytic performance, with 100% ethylene selectivity and 99.0% $U_{CO_2}$ under optimized conditions. The combined results of XAS, AP-XPS, and DFT studies show that the electronic properties and catalytic activity of ZnCr/SSZ-13 can be assigned to unique atomic synergies between neighboring Zn and Cr atoms resulting from colocalization. The redox Cr site facilitates the formation of $Zn^{\delta+}$, which is the active site for easier adsorption and activation of both ethane and $CO_2$. Further, the Cr site accelerates $CO_2$ dissociation, due to its redox properties, and facilitates the formation and desorption of $H_2O$. This combination results in rate matching between ethane dehydrogenation and $CO_2$ hydrogenation. This highlights the importance of atomic synergy, providing guidance for developing novel catalysts with potential economic and ecological benefits in $CO_2$ conversion and olefin production.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A method comprising:

mixing a Zn precursor, a metal precursor, and a zeolite to form a mixture;

grinding the mixture; and after grinding the mixture, heat treating the mixture to form a Zn3M1/zeolite catalyst, wherein M is a metal selected from the group consisting of Cr, Mo, and W, and wherein Zn and M form at least some $ZnMO_x$ oxides.

2. The method of claim 1, wherein the zeolite comprises at least one of HSSZ-13 zeolite, NaSSZ-13 zeolite, HZSM-5 zeolite, NaZSM-5 zeolite, H-ZSM-11 zeolite, H-ZSM-22 zeolite, H-ZSM-23 zeolite, ZSM-35 zeolite, Beta zeolite, SAPO-11 zeolite, or SAPO-34 zeolite.

3. The method of claim 1, wherein the Zn precursor comprises at least one of zinc (II) acetate, zinc (II) nitrate, or zinc (II) chloride, and wherein the metal precursor comprises at least one of chromium (III) acetate hydroxide, chromium (III) nitrate, chromium (III) chloride, ammonium molybdate tetrahydrate, or ammonium metatungstate hydrate.

4. The method of claim 1, wherein grinding the mixture is performed with a ball mill.

5. The method of claim 1, wherein the Zn precursor and the metal precursor each have a particle size of less than about 0.5 nanometers after the grinding.

6. The method of claim 1, wherein the zeolite has a particle size of about 1 micron to 2 microns after the grinding.

7. The method of claim 1, wherein the heat treating comprises heating the mixture to about 300° C. to 800° C. for about 1.5 hours to 4.5 hours.

8. The method of claim 1, wherein the Zn3M1/zeolite catalyst comprises Zn3Cr1/SSZ-13 catalyst.

9. The method of claim 1, further comprising: prior to the mixing, dehydrating the zeolite.

10. The method of claim 9, wherein the dehydrating comprises heating the zeolite to about 60° C. to 180° C. for about 1.5 hours to 4.5 hours while under a vacuum.

11. The method of claim 1, further comprising:

after the heat treating, neutralizing the surface acidity of the zeolite.

12. The method of claim 11, wherein neutralizing the surface acidity of the zeolite comprises $Na^+$-neutralizing the zeolite comprising dispersing the mixture in deionized water to form a suspension, adding a sodium bicarbonate solution to the suspension so that the suspension has a pH of about 7, and removing the mixture from the suspension.

13. A Zn3M1/zeolite catalyst, with M being a metal selected from the group consisting of Cr, Mo, and W, and at least some $ZnMO_x$ oxides.

14. The Zn3M1/zeolite catalyst of claim 13, wherein the Zn3M1/zeolite catalyst comprises a zeolite with Zn oxide nanoparticles, M oxide nanoparticles, and $ZnMO_x$ oxide nanoparticles disposed on the zeolite.

15. The Zn3M1/zeolite catalyst of claim 14, wherein the Zn oxide nanoparticles, M oxide nanoparticles, and $ZnMO_x$ oxide nanoparticles have particle sizes of about 0.5 nanometers to 1 nanometer.

16. The Zn3M1/zeolite catalyst of claim 13, wherein the zeolite comprises at least one of HSSZ-13 zeolite, NaSSZ-13 zeolite, HZSM-5 zeolite, NaZSM-5 zeolite, H-ZSM-11 zeolite, H-ZSM-22 zeolite, H-ZSM-23 zeolite, ZSM-35 zeolite, Beta zeolite, SAPO-11 zeolite, or SAPO-34 zeolite.

17. The Zn3M1/zeolite catalyst of claim 13, wherein the Zn3M1/zeolite catalyst comprises Zn3Cr1/SSZ-13.

18. A method comprising:

providing a Zn3M1/zeolite catalyst, with M being a metal selected from the group consisting of Cr, Mo, and W, and at least some $ZnMO_x$ oxides;

heating the Zn3M1/zeolite catalyst to about 400° C. to 650° C.; and flowing carbon dioxide and ethane through the Zn3M1/zeolite catalyst and generating carbon monoxide and ethylene.

19. The Zn3M1/zeolite catalyst of claim 13, wherein Zn comprises an oxide.

20. The Zn3M1/zeolite catalyst of claim 13, wherein M comprises an oxide.

21. The Zn3M1/zeolite catalyst of claim 13, wherein the Zn3M1/zeolite catalyst comprises Zn3Cr1/zeolite.

22. The Zn3M1/zeolite catalyst of claim 13, wherein the Zn3M1/zeolite catalyst comprises at least one of Zn3Mol/zeolite or Zn3W1/zeolite.

* * * * *